United States Patent [19]

Nishiyama et al.

[11] 4,184,041
[45] Jan. 15, 1980

[54] 2-SUBSTITUTED-5-TRIFLUOROMETHYL-PYRIDINE COMPOUNDS

[75] Inventors: Ryuzo Nishiyama, Takatsuki; Kanichi Fujikawa, Kusatsu; Takahiro Haga, Kusatsu; Kuniaki Nagatani, Kusatsu, all of Japan

[73] Assignee: Ishihara Sangyo Kaisha Ltd., Osaka, Japan

[21] Appl. No.: 889,074

[22] Filed: Mar. 22, 1978

[30] Foreign Application Priority Data

Oct. 21, 1977 [JP] Japan ................. 52-126489

[51] Int. Cl.$^2$ ........................... C07D 213/61
[52] U.S. Cl. ........................... 546/345; 71/94
[58] Field of Search .............. 260/290 HL; 560/345

[56] References Cited
U.S. PATENT DOCUMENTS

| | | | |
|---|---|---|---|
| 2,516,402 | 7/1950 | McBee et al. | 260/290 HL |
| 3,755,329 | 8/1973 | Vaughan | 260/270 R |
| 4,038,396 | 7/1977 | Shen et al. | 424/256 |

OTHER PUBLICATIONS

Tewksbury et al., J. Am. Chem. Soc., 71, 2336–2337 (1949).

Primary Examiner—Alan L. Rotman
Assistant Examiner—Bernard Dentz
Attorney, Agent, or Firm—Sughrue, Rothwell, Mion, Zinn and Macpeak

[57] ABSTRACT

A 2-substituted-5-trifluoromethylpyridine compound represented by the following general formula (I):

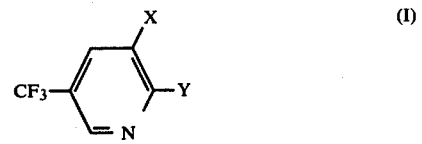

wherein X represents a hydrogen atom or a chlorine atom, and Y represents a fluorine atom or a chlorine atom, and a process for the preparation thereof.

3 Claims, No Drawings

2-SUBSTITUTED-5-TRIFLUOROMETHYLPYRIDINE COMPOUNDS

BACKGROUND OF THE INVENTION

1. Field of the Invention

This invention relates to novel 2-substituted-5-trifluoromethylpyridine compounds useful as intermediates in the production of medicines, agricultural chemicals, dyes, etc.

2. Description of the Prior Art

Trifluoromethylpyridine type compounds having an analogous chemical structure to that of the compounds of this invention described herein are well known as described in, for example, U.S. Pat. No. 3,755,329. However, these pyridine type compounds can not be easily prepared on an industrial scale.

SUMMARY OF THE INVENTION

The present invention provides a 2-substituted-5-trifluoromethylpyridine compound represented by the following general formula (I):

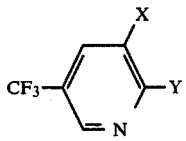

wherein X represents a hydrogen atom or a chlorine atom, and Y represents a fluorine atom or a chlorine atom.

The present invention also provides a process for preparing the compounds of the general formula (I).

DETAILED DESCRIPTION OF THE INVENTION

The 2-substituted-5-trifluoromethylpyridine compounds represented by the general formula (I) of the present invention can be prepared by fluorinating a compound represented by the general formula (II) to produce the compound represented by the general formula (I) according to, for example, the following reaction scheme (I).

Reaction Scheme (1)

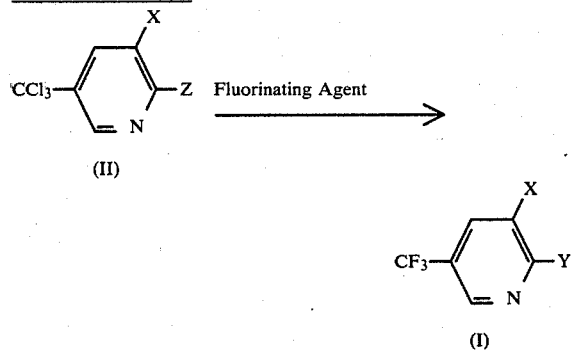

In the above reaction scheme (1), X and Y are the same as defined above, and Z represents a halogen atom with a fluorine atom, a chlorine atom and a bromine atom being preferred.

Where hydrogen fluoride is used as the fluorinating agent, the reaction is completed in 1 to 72 hours by treating the compound represented by the general formula (V) with gaseous hydrogen fluoride at 0° to 50° C. Upon conducting the reaction, an appropriate solvent may be used, if necessary.

Where metal fluorides such as antimony trifluoride are used as the fluorinating agents, the reaction is completed in 5 minutes to 1 hour by mixing the starting material, the compound represented by the general formula, (II), with, e.g., antimony trifluoride, and heating the resulting mixture at 100° to 250° C. In addition, the end product, the 2-substituted-5-trifluoromethylpyridine compound represented by the general formula (I), can be also obtained by heating and vaporizing the starting material, the 2-substituted-5-trichloromethylpyridine compound represented by the general formula (II), and reacting the vaporized starting material with a metal fluoride at an elevated temperature.

The compound represented by the general formula (II) can be produced by chlorinating, under ultraviolet light irradiation, a compound represented by the general formula (III):

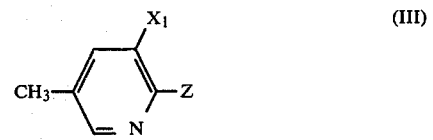

wherein $X_1$ represents a hydrogen atom, a chlorine atom or a bromine atom, and Z is the same as defined hereinbefore, which can be produced by diazotizing 2-amino-5-methylpyridine with or without prior halogenation.

The 2-substituted-5-trifluoromethylpyridine compound represented by the general formula (I) can also be prepared by reacting a compound represented by the general formula (IV) with a compound represented by the general formula (V) according to reaction scheme (2) below.

Reaction Scheme (2)

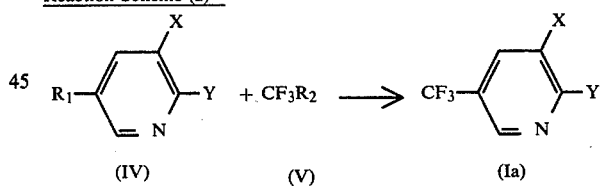

In the above reaction scheme (2), X and Y are the same as defined in the general formula (I), and $R_1$ and $R_2$ each represents a bromine atom or an iodine atom.

The reaction is conducted for 5 to 24 hours at 100° to 200° C. in the presence of copper dust and a solvent, for example, a polar aprotic solvent such as pyridine, sulfolane, dimethylformamide, dimethyl sulfoxide, etc.

The starting materials described in the above methods are known in the art. For example, 2-amino-5-methylpyridine is disclosed in *Chemical Abstracts,* Vol. 43, 7050i; (1949) compounds of the general formula (IV) are described in U.S. Pat. No. 4,046,553; and compounds of the general formula (V) are described in *Org. Reaction,* Vol. 9, p. 358.

The compounds of the present invention represented by the general formula (I) can be converted to 4-(5-trifluoromethylpyridyl-2-oxy)phenoxyalkanecarboxylic acids, 4-(3-halogen substituted-5-trifluoromethylpyridyl-2-oxy)phenoxyalkanecarboxylic acids, the esters or the amides of these acids, etc., by reacting them with a p-hydroxyphenoxyalkanecarboxylic acid, a p-hydroxyphenoxyalkanecarboxylic acid ester or amide thereof or the like. These reactions are conducted at 50° C. or above for 1 to 20 hours in the presence of an alkaline material. A suitable alkaline material which can be used is an alkali metal hydroxide or an alkali metal carbonate such as sodium hydroxide, potassium hydroxide, sodium carbonate, potassium carbonate, etc. These reactions may be conducted in the presence of a polar aprotic solvent, e.g., as described above.

The above-described compounds produced from the compounds of the present invention represented by the general formula (I) show an excellent activity as active ingredients of, for example, agricultural chemicals, in particular, herbicides. Above all, selective herbicidal activity in withering gramineous weeds without substantial damage to crops in fields where broad-leaved crops such as cotton, soybeans, etc., are cultivated is noteworthy as a specific activity. Gramineous weeds which are selectively affected by these compounds produced from the compounds of the present invention represented by the general formula (I) include barnyard grass (*Echinochloa crus-galli* BEAUV.), large crabgrass (*Digitaria adscendens* HENR.), green foxtail (*Setaria viridis* BEAUV.), etc. The above-described compounds exhibit a distinct selective herbicidal activity on these gramineous weeds using either a pre-emergence soil treatment or a post-emergence foliage treatment. The degree of growth inhibition in the case of spraying, for example, 50 g per are (100 m$^2$) as an active ingredient was evaluated on a scale of 10 grades in which 10 indicates that growth was completely inhibited and 1 indicates no inhibition; the degree of growth inhibition of broad-leaved crops was 1 to 2, whereas the degree of growth inhibition of gramineous weeds was 9 to 10.

Representative examples of the preparation of the compounds of the present invention represented by the general formula (I) are described below. Unless otherwise indicated herein, all parts, percents, ratios and the like are by weight.

EXAMPLE 1

Preparation of 2-Chloro-5-trifluoromethylpyridine

Preparation (1)

216 g of 2-amino-5-methylpyridine was added to 1 l of 47% hydrobromic acid kept at 10° to 20° C., and 300 ml of bromine was added to the mixture at 0° C. Thereafter, the temperature of the system was decreased to 0° C. or less, and a solution of 350 g of sodium nitrite dissolved in 500 ml of water was added dropwise to the system. After a lapse of 30 minutes, a solution of 750 g of sodium hydroxide dissolved in 750 ml of water was added to the resulting system at a temperature of 25° C. or less.

The thus obtained reaction product was extracted with toluene, and the extract was washed successively with a 5% sodium hydroxide aqueous solution and water, followed by drying over anhydrous sodium sulfate. Then, the toluene was distilled off to obtain 315 g of 2-bromo-5-methylpyridine with a melting point of 39° to 39.5° C.

172 g of thus obtained 2-bromo-5-methylpyridine was dissolved in 1.3 l of carbon tetrachloride, and the system was then heated. At the time refluxing begain (at 77° C.), chlorine gas was bubbled into the system with ultraviolet light irradiation. After a lapse of 5 hours, the completion of the reaction was confirmed by gas chromatography, and the system was cooled and air was bubbled into the system to expel the unreacted chlorine. The system was washed with water several times and dried over anhydrous sodium sulfate. Then, the carbon tetrachloride was distilled off, and the system was allowed to cool. The solid crystals thus-obtained were washed with n-hexane to obtain 152 g of 2-chloro-5-trichloromethylpyridine with a melting point of 51° to 54° C.

23.1 g of 2-chloro-5-trichloromethylpyridine and 17.9 g of antimony trifluoride were mixed in a flask equipped with a thermometer, a stirrer and a reflux condenser. The reaction was initiated immediately when the mixture was heated to 170° C., and a formed low boiling product began to be refluxed. Five minutes after the initiation of the reflux, the condenser was directed downward to distill out the refluxing product. The distillate was extracted with methylene chloride, and the extract was washed successively with 10% dilute hydrochloric acid and water and, after drying over anhydrous sodium sulfate, the washed extract was concentrated. The concentrate was distilled to obtain 8.0 g of 2-chloro-5-trifluoromethylpyridine with a boiling point of 91°–93° C./80 mmHg.

Preparation (2)

In an autoclave were placed 2.9 g of 2-chloro-5-iodopyridine, 2.5 g of trifluoromethyl bromide dissolved in 100 ml of pyridine and 1.6 g of copper dust, and the mixture was reacted at 170° C. for 18 hours. After cooling the system, the reaction mixture was added to a suitable amount of water and extracted with methylene chloride. The extract was washed successively with water, 10% dilute hydrochloric acid, and water. After drying over anhydrous sodium sulfate, the extract was distilled to remove the methylene chloride and obtain 300 mg of 2-chloro-5-trifluoromethylpyridine.

The thus-obtained 2-chloro-5-trifluoromethylpyridine can be converted to ethyl α-[4-(5-trifluoromethylpyridine-2-oxy)phenoxy]propionate using the following procedures.

9.1 g of 2-chloro-5-trifluoromethylpyridine and 21.0 g of ethyl α-(4-hydroxyphenoxy)propionate were dissolved in 50 ml of dimethyl sulfoxide, and 13.8 g of anhydrous potassium carbonate was added thereto. The reaction was conducted for 2 hours at 150° C. with stirring. The reaction product was cooled and then added to ice-water, followed by extracting the solid material with toluene. The toluene phase was washed several times with water, and dried over anhydrous sodium sulfate. Then, the toluene was distilled off to obtain 12.4 g of an oily product (I).

On the other hand, the aqueous phase was washed with toluene, and acidified with 30% concentrated hydrochloric acid to obtain an oily material. This oily material was extracted with methylene chloride, washed well with water, and dried over anhydrous sodium sulfate, followed by distilling off the methylene chloride to obtain 9.0 g of an oily material. This oily material was mixed with an excess amount of ethanol and, after adding thereto 2 ml of a diethyl ether solution of boron trifluoride, the mixture was refluxed (80° C.) for 2 hours. Then, a slight amount of water was added thereto, and the ethanol was distilled off. The resulting oil was extracted with methylene chloride, washed with water, and dried over anhydrous sodium sulfate. After distilling off the methylene chloride, 6.0 g of an oily material (II) was obtained.

Oily materials (I) and (II) were combined and adsorbed on a silica gel column, followed by eluting with toluene. After distilling off the toluene from the eluate, 11.6 g of an oily material was obtained. This material was solidified by cooling, then washed with n-hexane and dried to obtain 6.5 g of ethyl α-[4-(5-trifluoromethylpyridyl-2-oxy)phenoxy]propionate.

EXAMPLE 2

Preparation of 2-Fluoro-5-trifluoromethylpyridine 27.6 g of 2-bromo-5-trichloromethylpyridine was mixed with 17.9 g of antimony trifluoride in a flask equipped with a thermometer, a stirrer and a reflux condenser. Upon heating to 150° to 180° C., the reaction was immediately initiated and a formed low boiling product began to be refluxed. 20 minutes after the initiation of the reflux, the condenser was directed downward to distill out the refluxed product. The distillate was extracted with methylene chloride, and the extract was washed successively with water, 15% dilute hydrochloric acid, and water. After drying, the washed extract was concentrated and distilled to obtain 5.3 g of the title product having a boiling point of 115°–120° C.

EXAMPLE 3

Preparation of 2,3-Dichloro-5-trifluoromethylpyridine

The same procedures as described in Example 1, Preparation (1) above were repeated except for using 26.6 g of 2,3-dichloro-5-trichloromethylpyridine in place of 23.1 g of 2-chloro-b 5-trichloromethylpyridine. After the post-treatment, 7.7 g of the title product having a boiling point of 98°–101° C./70 mmHg was obtained.

While the invention has been described in detail and with reference to specific embodiments thereof, it will be apparent to one skilled in the art that various changes and modifications can be made therein without departing from the spirit and scope thereof.

What is claimed is:

1. A 2-substituted-5-trifluoromethylpyridine compound represented by the following formula (I):

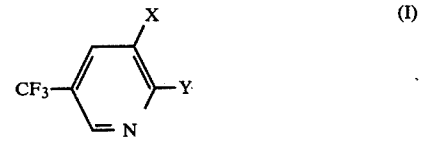

wherein X represents a chlorine atom, and Y represents a fluorine atom or a chlorine atom.

2. 2-Fluoro-5-trifluoromethylpyridine.
3. 2,3-Dichloro-5-trifluoromethylpyridine.

* * * * *